US008793074B2

(12) United States Patent
Aurora et al.

(10) Patent No.: US 8,793,074 B2
(45) Date of Patent: Jul. 29, 2014

(54) SEQUENCE COVARIANCE NETWORKS, METHODS AND USES THEREFOR

(75) Inventors: Rajeev Aurora, Wildwood, MO (US); Maureen J. Donlin, Kirkwood, MO (US); John E. Tavis, Kirkwood, MO (US)

(73) Assignee: Saint Louis University, St. Louis, MO (US)

(*) Notice: Subject to any disclaimer, the term of this patent is extended or adjusted under 35 U.S.C. 154(b) by 418 days.

(21) Appl. No.: 12/144,030

(22) Filed: Jun. 23, 2008

(65) Prior Publication Data

US 2008/0318207 A1    Dec. 25, 2008

Related U.S. Application Data

(60) Provisional application No. 60/945,543, filed on Jun. 21, 2007, provisional application No. 60/897,696, filed on Nov. 13, 2007.

(51) Int. Cl.
*G06F 19/22* (2011.01)
*G06F 19/24* (2011.01)
*G06F 19/00* (2011.01)
*A61K 38/21* (2006.01)
*A61K 31/7056* (2006.01)

(52) U.S. Cl.
CPC ............... *G06F 19/22* (2013.01); *G06F 19/24* (2013.01); *G06F 19/3443* (2013.01); *G06F 19/3456* (2013.01); *A61K 38/212* (2013.01); *A61K 31/7056* (2013.01)
USPC .......................................................... 702/19

(58) Field of Classification Search
None
See application file for complete search history.

(56) References Cited

U.S. PATENT DOCUMENTS

2002/0091664 A1* 7/2002 Larder et al. ..................... 702/19
2002/0127203 A1* 9/2002 Albrecht ...................... 424/85.7

OTHER PUBLICATIONS

Aurora, R., Donlin, M. J., Cannon, N. A. & Tavis, J. E. Genome-wide hepatitis c virus amino acid covariance networks can predict response to antiviral therapy in humans. Journal of Clinical Investigation 119, 225-236 (2008).*
Chou, S., Lurain, N. S., Thompson, K. D., Miner, R. C. & Drew, W. L. Viral dna polymerase mutations associated with drug resistance in human cytomegalovirus. The Journal of infectious diseases 188, 32-39 (2003).*

(Continued)

*Primary Examiner* — Soren Harward
(74) *Attorney, Agent, or Firm* — Armstrong Teasdale LLP

(57) ABSTRACT

Methods of identifying targets for designing a therapeutic agent are disclosed. These methods comprise: determining an amino acid sequence of one or more polypeptides of each isolate of a plurality of isolates of a biological system; identifying covariance pairs of amino acid residues; establishing a network comprising the covariance pairs; and identifying one or more hub residue positions, wherein a hub residue position comprises a target for designing a therapeutic agent if the hub residue position has a rank order in the $40^{th}$ percentile or greater. In other aspects, methods are disclosed for selecting a therapy for an infectious disorder. In various configurations, these methods comprise: determining amino acids occupying a plurality of diagnostic amino acid residue positions comprised by one or more polypeptides encoded by an infectious agent infecting a subject; and assigning the infectious agent infecting the subject to one covariance network selected from a plurality of covariance networks, wherein each network comprises a unique rank order of hubs with respect to the other networks, and whereby the therapy is selected on the basis of the covariance network assignment.

8 Claims, 6 Drawing Sheets

(56) References Cited

OTHER PUBLICATIONS

Hammond, J., Calef, C., Larder, B., Schinazi, R. & Mellors, J. W. Mutations in retroviral genes associated with drug resistance. In Korber, B., Foley, B. & McCutchan, F. (eds.) Human Retroviruses and AIDS 1998, III36-III79 (Los Alamos National Laboratory, 1998).*

Hoffman, N. G., Schiffer, C. A. & Swanstrom, R. Covariation of amino acid positions in HIV-1 protease. Virology 314, 536-548 (2003).*

Shafer, R. W. Genotypic testing for human immunodeficiency virus type 1 drug resistance. Clinical microbiology reviews 15, 247-277 (2002).*

Enomoto, N. et al. Comparison of full-length sequences of interferon-sensitive and resistant hepatitis C virus 1b. Sensitivity to interferon is conferred by amino acid substitutions in the NS5A region. The Journal of Clinical Investigation 96, 224-230 (1995).*

Manns, M. et al. Peginterferon alfa-2b plus ribavirin compared with interferon alfa-2b plus ribavirin for initial treatment of chronic hepatitis C: a randomised trial. The Lancet 358, 958-965 (2001).*

Wu, T. D. et al. Mutation Patterns and Structural Correlates in Human Immunodeficiency Virus Type 1 Protease following Different Protease Inhibitor Treatments. J. Virol. 77, 4836-4847 (2003).*

Ghedin, E. et al. Large-scale sequencing of human influenza reveals the dynamic nature of viral genome evolution. Nature 437, 1162-6 (2005).*

"Antiviral Drugs" from The Gale Encyclopedia of Medicine. (Gale Group, 2002).*

Donlin, M. J., Szeto, B., Gohara, D. W., Aurora, R. & Tavis, J. E. Genome-wide networks of amino acid covariances are common among viruses. J. Virol. 86, 3050-3063 (2012).*

Nijhuis, M. et al. Increased fitness of drug resistant HIV-1 protease as a result of acquisition of compensatory mutations during suboptimal therapy. AIDS 13, 2349-2359 (1999).*

Zhang, Y. et al. Drug resistance during indinavir therapy is caused by mutations in the protease gene and in its Gag substrate cleavage sites. J. Virol. 71, 6662-6670 (1997).*

Albert and Barabasi, Topology of evolving networks: local events and universality, Phys Rev Lett, 2000, p. 5234-5237, vol. 85.

Altschuh et al, Correlation of co-ordinated amino acid substitutions with function n viruses related to tobacco mosaic virus, J Mol Bio, 1987, p. 693-707, vol. 193.

Atchley et al, Correlations among amino acid sites in bHLH protein domains: an information theoretic analysis, Mol Biol Evol, 2000, p. 164-178, vol. 17.

Bukh et al, Genetic heterogeneity of hepatitis C viruses: quasispecies and genotypes, Semin Liver Dis, 1995, p. 41-63, vol. 15.

Donlin et al, Pretreatment sequence diversity differences in the full-length hepatitis C virus open reading frame correlate with early response to therapy, J virol, 2007, p. 8211-8224, vol. 81.

Fodor and Aldrich, Influence of conservation on calculations of amino acid covariance in multiple sequence alignments, Proteins, 2004, p. 211-221, vol. 56.

Jeanmougin et al, Multiple sequence alignment with CLUSTAL X, Trends Biochem Sci, 1998, p. 403-405, vol. 23.

Kass and Horovitz, Mapping pathways of allosteric communication in GroEL by analysis of correlated mutations, Proteins, 2000, p. 611-617, vol. 48.

Kurosaki et al, Evolution and selection of hepatitis C virus variants in patients with chronic hepatitis C, Virology, 1994, p. 161-169, vol. 205.

Larson and Davidson, The identification of conserved interactions within the SH3 domain by alignment of sequences and structures, Protein Sci, 2000, p. 2170-2180, vol. 9.

Larson et al, Analysis of covariation in an SH3 domain sequence alignment: applications in tertiary contact prediction and the design of compensating hydrophobic core substitutions, J Mol Biol, 2000, p. 433-446, vol. 303.

Olmea and Valencia, Improving contact predictions by the combination of correlated mutations and other sources of sequence information, Fold Des, 1997, p. S25-S32, vol. 2.

Olmea et al, Effective use of sequence correlation and conservation in fold recognition, J Mol Biol, 1999, p. 1221-1239, vol. 293.

Penin, Structural biology of hepatitis C virus, Clin Liver Dis, 2003, p. 1-21, vol. 7.

Robertson et al, Classification, nomenclature, and database development for hepatitis C virus (HCV) and related viruses: proposals for standardization; International Committee on Virus Taxonomy, Arch Virol, 1998, p. 2493-2503, vol. 143.

Shannon et al, Cytoscape: A software environment for integrated models of biomolecular interaction networks, Genome Res, 2003, p. 2498-2504, vol. 13.

Simmonds et al, Classification of hepatitis C virus into six major genotypes and a series of subtypes by phylogenetic analysis of the NS-5 region, J General Virol, 1993, p. 2391-2399, vol. 74.

Simmonds, Genetic diversity and evolution of hepatitis C virus—15 years on, J General Virol, 2004, p. 3173-3188, vol. 85.

Thomas et al, The prediction of protein contacts from multiple sequence alignments, Protein Eng, 1996, p. 941-940, vol. 9.

Wang and Delisi, Inferring protein-protein interactions in viral proteins by co-evolution of conserved side chains, Genome Inform, 2006, p. 23-35, vol. 17.

Zeuzem, Hepatitis C virus: kinetics and quasispecies evolution during anti-viral therapy, Forum (Genova), 2000, p. 32-42, vol. 10.

M. Basson, "Heads up on HCV," Nature Medicine, Feb. 2009, 15(2):148-149.

Oh, T.S., and Rice, C.M., "Predicting response to hepatitis C therapy," J. Clin. Invest., 2009, 119(1):5-7.

Nattermann, J., and Tacke, F., Hepatology, May 2009, 49(5):1767-1769.

* cited by examiner

SEQUENCE COVARIANCE NETWORKS, METHODS AND USES THEREFOR

STATEMENT OF GOVERNMENT SUPPORT

This invention was made with government support under NIH Grant UOI DK60345 awarded by the National Institute of Diabetes and Digestive and Kidney Diseases and under RO1 CA 126807 awarded by the National Cancer Institute. The Government has certain rights in the invention.

CROSS REFERENCE TO RELATED APPLICATIONS

This application claims the benefit of priority to U.S. Provisional Application 60/945,543 filed Jun. 21, 2007, and U.S. Provisional Application 60/987,696 filed Nov. 13, 2007. Each of these applications is incorporated herein by reference in its entirety.

INTRODUCTION

This patent is in the field of systems biology.

About 3.8 million Americans are chronically infected with Hepatitis C virus (HCV), and the Centers for Disease Control and Prevention estimate that hepatitis C causes 8,000-10,000 deaths each year in the USA. Currently, the best therapy for HCV infection is a combination of pegylated interferon α and ribavirin, a guanosine analogue. Treatment with these drugs for 24 to 48 weeks leads to sustained clearance of the virus and stabilization of liver function in 50-60% of genotype 1 patients (Manns, M. P., et al., Lancet 358, 958-965, 2001; Hadziyannis, S. J., et al., Ann. Intern. Med. 140, 346-355, 2004). IFN α provides the primary antiviral effect during therapy and can clear HCV even when used alone (Poynard, T., et al., Lancet 352, 1426-1432, 1998; McHutchison, J. G., et al., New England J. Med. 339, 1485-1492, 1998). Ribavirin cannot eliminate viremia by itself (Bodenheimer, H. C., et al., Hepatology 26, 473-477, 1997; Dusheiko, G., et al., J. Hepatol. 25, 591-598, 1996; Di Bisceglie, A. M., et al., Ann. Intern. Med. 123, 897-903 1995), although it can reduce viral titres slightly in some patients (Pawlotsky, J. M., et al., Gastroenterology 126, 703-714, 2004). When ribavirin is taken in combination with IFN α, it roughly doubles the viral clearance rate (McHutchison, J. G., et al., New England Journal of Medicine 339, 1485-1492, 1998; Poynard, T., et al., Lancet 352, 1426-1432, 1998; Davis, G. L., et al., New England J. Med. 339, 1493-1499, 1998), apparently by reducing relapse following the end of drug treatment. Unfortunately, there are no effective therapies for patients who fail to clear virus following IFN α plus ribavirin therapy.

The HCV genome is a ~9,600 nucleotide long RNA that encodes a single polyprotein of ~3010 amino acids (FIG. 1). The polyprotein is post-translationally cleaved by host and viral proteases to produce ten mature viral proteins. The core, E1, and E2 proteins form the virion, and P7-NS5B are non-structural proteins with regulatory and/or enzymatic functions. The HCV genome is highly variable, and six HCV genotypes that are less than 72% identical at the nucleotide level have been identified (Simmonds, P. et al., J. General Virol. 74, 2391-2399, 1993; Bukh, J., et al., Seminars in Liver Disease 15, 41-63, 1995; Robertson, B., et al., Archives Virol. 143, 2493-2503, 1998; Simmonds, P., et al., Hepatology 42, 962-973, 2005; Simmonds, P., J. Gen. Virol. 85, 3173-3188, 2004). Within these genotypes, subtypes with identities of 75-86% may occur. HCV replicates as a quasispecies rather than as a clonal population, and hence multiple closely-related HCV variants exist within individual patients. The quasispecies develops because the viral production rate is very high [about $10^{12}$ virions per day; (Neumann, A. U., et al., Science 282, 103-107 1998)] and the viral RNA polymerase has low fidelity. Therefore, new mutations are constantly introduced into the viral pool, and each of these variant genomes is in competition with the others (Kurosaki, M. et al., Virology 205, 161-169, 1994; Zeuzem, S., Forum (Genova) 10, 32-42, 2000). The result is that at any given time, one or a few genomes will be dominant because they are most fit for the prevailing conditions, as defined by host physiology, immune status, and antiviral drug challenge. The quasispecies distribution can vary with time through adaptive or neutral evolution (Simmonds, P., J. Gen. Virol. 85, 3173-3188, 2004). Adaptive changes are due to emergence of more fit variants as conditions facing the virus change. Neutral changes result from replacement of sequences with others of equivalent fitness. The high genetic variability of HCV has two fundamental biological effects. First, it provides diversity for rapid viral evolution in response to selective pressures, such as an immune response or antiviral pressure. Second, the diversity causes many viral genomes to contain variations that are either lethal or reduce fitness, leading to their loss from the viral population.

The Viral Resistance to Antiviral Therapy of Chronic Hepatitis C clinical study (Virahep-C) recently investigated the efficacy of pegylated IFN α plus ribavirin for treating hepatitis C (Conjeevaram, H. S., et al., Gastroenterology 131, 470-477, 2006.). As part of Virhahep-C, the inventors performed a viral genetics study to identify viral genetic patterns associated with response or failure of therapy and to determine which viral genes are targets of antiviral pressures induced by therapy (Donlin, M. J., et al., J. Virol. 81, 8211-8224, 2007). The inventors sequenced the complete HCV ORF from 94 patients before therapy, stratified based on response to therapy at day 28 (Marked, Intermediate, or Poor responders) and genotype (1a or 1b). The inventors found that viral genetic variability in sequences from the marked responders (in whom therapy efficiently suppressed viral titres) was much higher than in the poor responders (in whom suppression of the virus was minimal or absent). These genetic variability differences were found primarily in the viral NS3 and NS5A genes for genotype 1a and in core and NS3 for genotype 1b. Importantly, core, NS3, and NS5A all have functions in cultured cells that can counteract the effect of interferon α, the dominant drug during HCV therapy (Gale, M., and Foy, E. M., Nature 436, 939-945, 2005). The inventors interpreted the association of higher diversity with response to therapy to imply that virus in the poor responders survived because there are only a few ways to optimize activity of the viral proteins, but many ways to interfere with their function.

The inventor's previous results were from position-based analyses of amino acid alignments, and did not take into account potential linkages of the genetic variations at multiple locations within the viral coding sequences. Correlated variations identified from multiple sequence analyses can be used to predict residue contacts in proteins (Altschuh, D., et al., J. Mol. Biol. 193, 693-707, 1987; Larson, S. M., and Davidson, A. R., Protein Sci. 9, 2170-2180, 2000; Larson, S. M., et al., J. Mol. Biol. 303, 433-446, 2000; Olmea, O., et al., J. Mol. Biol. 293, 1221-1239, 1999; Olmea, O., and Valencia, A., Fold. Des. 2, S25-S32, 1997; Thomas, D. J., et al., Protein Engineering 9, 941-948, 1996), and also to infer protein-protein interactions (Wang, Y. E., and DeLisi, C., Gennome Inform. 17, 23-35, 2006).

SUMMARY

In view of the need for new therapies and diagnostic methods, the present inventors have developed novel methods for developing pharmaceutical agents, selecting therapies and identifying targets for designing therapeutic agents such as small molecule drugs, peptides and antibodies. The methods they have developed can, in principle, be applied to any biological system for which sequence information can be obtained, in particular polypeptide sequence information. The methods can be applied at various taxonomic levels, e.g., to a species, a quasispecies, a subspecies, a strain, or to a higher taxonomic division, such as a genus, family or order.

In various aspects of the present teachings, biological systems to which the disclosed methods can be applied include, without limitation, viruses, including viruses that infect mammals including viruses that infect humans, and viruses that infect plants, such as tobacco mosaic virus, cucumber mosaic virus, and tomato wilt virus. Some non-limiting examples of viruses to which the disclosed techniques can be applied include RNA viruses and DNA viruses, such as: positive-polarity single-stranded RNA viruses including Flaviviridae, such as Yellow fever virus, Dengue virus, West Nile virus, Japanese encephalitis virus, a Hepacivirus such as a Hepatitis C virus, including subtypes such as such as a Hepatitis C virus subtype 1a or a Hepatitis C virus subtype 1b, and reverse-transcribing retroviruses such as HIV-1 and HIV-2; negative polarity segmented RNA viruses such as Influenza virus, strains of which infect humans or animals such as birds or swine (and can cause massive repetitive pandemics with millions of infections and deaths per pandemic); negative polarity unsegmented RNA viruses including Paramyxoviridae such as Measles virus, Respiratory Syncytial virus, and Mumps virus, as well as Rhabdoviridae such as rabies virus; positive-polarity single-stranded RNA viruses including Picornaviridae such as rhinovirus (which causes the common cold, and for which over 100 strains are known), Enteroviruses (which can cause gastroenteritis and hepatitis) such as Coxsackie virus, Echovirus, Hepatitis A virus, and Foot-and-mouth disease virus; double-stranded segmented RNA viruses, including Rotaviridae (which can cause severe diarrhea and gastroenteritis, especially in children); partially double-stranded DNA viruses including Hepadnaviridae such as Hepatitis B virus (which infects 350 million people world-wide and kills 1,000,000 people per year through liver failure and liver cancer); mixed positive and negative polarity single-stranded DNA viruses, including Parvoviridae such as Canine and Feline Parvoviruses; Double stranded DNA viruses, including Herpesviridae such as Herpes viruses (which can cause diseases such as cold-sores, venereal disease, and chicken-pox), Poxyiridae (causing smallpox) and Papillomaviridae including papilloma viruses (which can cause warts and cervical cancer). In some biological systems, such as DNA viruses, the methods can be applied to a subset of genes with homologs in multiple viruses of the same class.

Other biological systems to which the disclosed methods can be applied include a prokaryotic microorganism such as a bacterium, including an infectious or pathogenic bacterium, or a eukaryotic microorganism such as, but not limited to, a yeast such as a *Saccharomyces cerevisiae* or a *Schizosaccharomyces pombe*, and macroscopic organisms, including plants and animals. In some configurations, a plant can be an *Arabidopsis thaliana*, and an animal can be from any phylum, including, but not limited to, vertebrates, insects, and nematodes. Vertebrates can include fish such as a zebrafish (*Brachydanio rerio*), amphibians, reptiles, birds and mammals. Mammals to which the disclosed methods can be applied include, without limitation, humans and rodents such as rats and mice. Insects to which the disclosed methods can be applied include, without limitation, *Drosophila melangaster*. Nematodes to which the disclosed methods can be applied include, without limitation, *Caenorhabditis elegans*.

In various aspects, the present inventors disclose methods of identifying one or more targets for designing a therapeutic agent. In various configurations, these methods comprise: determining an amino acid sequence of one or more polypeptides of each isolate of a plurality of isolates of a biological system; identifying covariance pairs of amino acid residues; establishing a network comprising the covariance pairs; and identifying one or more hub residue positions, wherein a hub residue position is an amino acid residue position which exhibits covariance with multiple other amino acid residue positions, and as used herein, a hub residue position is a residue position exhibiting covariance with at least 5 other amino acid residue positions. In various aspects, a plurality of isolates can comprise at least 5 isolates. In various aspects, covariance pairs of amino acid residues can be identified using any method known to skilled artisans, including, but not limited to, application of known algorithms (e.g., Olmea, O., et al., J. Mol. Biol. 293, 1221-1239, 1999; Atchley, W. R., et al., Mol. Biol. Evol. 17, 164-178, 2000; Kass, I., and Horovitz, A., Proteins 48, 611-617, 2002). In various aspects, a hub residue position can comprise a target for designing a therapeutic agent if the hub residue position has a rank order in the $40^{th}$ percentile or greater within a network comprising the hub. Furthermore, in some aspects, identifying one or more targets for designing a therapeutic agent can comprise selecting a hub on the basis of its percentile ranking within a network.

In some other aspects, the present inventors disclose methods of designing an antiviral therapy. In various configurations, these methods comprise: determining an amino acid sequence of one or more viral polypeptides of each isolate of a plurality of isolates of a virus; identifying covariance pairs of amino acid residues; establishing a network comprising the covariance pairs; and identifying one or more hub residue positions, whereby a hub residue position comprises a target for designing an anti-viral therapy. In some configurations, these methods further comprise designing an antiviral agent which targets the hub residue position.

In yet other aspects, the inventors disclose methods of selecting an antiviral therapy. In various configurations, these methods include: determining amino acids occupying a plurality of diagnostic amino acid residue positions comprised by one or more polypeptides encoded by a virus infecting a subject; and assigning the virus infecting the subject to one covariance network selected from a plurality of covariance networks, each network comprising a unique rank order of hubs with respect to the other networks, whereby the therapy is selected on the basis of the covariance network assignment. In various configurations, these methods can further comprise identifying the plurality of covariance networks, wherein the identifying comprises: (i) determining an amino acid sequence of one or more viral polypeptides of each isolate of a plurality of isolates of a virus; (ii) identifying covariance pairs of amino acid residues; and (iii) identifying a plurality of hubs, thereby establishing a plurality of networks in which each network comprises a unique rank order of hubs. In some configurations, the plurality of covariance networks can comprise at least a first covariance network and a second covariance network. Furthermore, in some configurations at least one hub can be comprised by the first covariance network but not comprised by the second covariance network.

In yet other aspects, the inventors disclose methods of selecting a therapy for an infectious disorder. In various configurations, these methods comprise: determining amino acids occupying a plurality of diagnostic amino acid residue positions comprised by one or more polypeptides encoded by an infectious agent infecting a subject; and assigning the infectious agent infecting the subject to one covariance network selected from a plurality of covariance networks, wherein each network comprises a unique rank order of hubs with respect to the other networks, and whereby the therapy is selected on the basis of the covariance network assignment. In various configurations, these methods can further comprise identifying the plurality of covariance networks, wherein the identifying can comprise: (i) determining an amino acid sequence of one or more polypeptides of each isolate of a plurality of isolates of an infectious agent; (ii) identifying covariance pairs of amino acid residues; and (iii) identifying a plurality of hubs, thereby establishing a plurality of networks in which each network comprises a unique rank order of hubs. In addition, some configurations of these methods can further comprise selecting a therapy wherein the plurality of covariance networks comprise at least a first covariance network and a second covariance network, and furthermore, at least one hub can be comprised by the first covariance network but not comprised by the second covariance network.

In yet other aspects, the inventors disclose methods of selecting a therapy for a biological disorder. In various configurations, these methods comprise: determining amino acids occupying a plurality of diagnostic amino acid residue positions comprised by one or more polypeptides encoded by a biological system; and assigning the biological system to one covariance network selected from a plurality of covariance networks, each network comprising a unique rank order of hubs, whereby the therapy is selected on the basis of the covariance network assignment. In various aspects, these methods can further comprise identifying the plurality of covariance networks, wherein the identifying comprises: (i) determining an amino acid sequence of one or more polypeptides of each isolate of a plurality of isolates of the biological system; (ii) identifying covariance pairs of amino acid residues; and (iii) identifying a plurality of hubs, thereby establishing a plurality of networks in which each network comprises a unique rank order of hubs. In some configurations, the plurality of covariance networks can comprise at least a first covariance network and a second covariance network, and furthermore, at least one hub can be comprised by the first covariance network but not comprised by the second covariance network.

In yet other aspects, the inventors disclose methods of identifying functionally interacting amino acid residue positions comprised by one or more polypeptides comprised by a biological system. In various configurations, these methods comprise: determining an amino acid sequence of one or more polypeptides of each isolate of a plurality of isolates of the biological system; and identifying one or more hubs, wherein each hub comprises a plurality of covariance pairs of amino acids, whereby a covariance pair is indicative of functional interactions between the amino acids comprising the covariance pair. In some configurations, the methods can further include: establishing a network comprising the one or more hubs, and assigning each hub a rank order within the network, wherein the rank order is determined by the number of edges for each hub, and "edge" as used herein refers to a covariance between pairs of amino acid positions with an observed minus expected square score ("OMES score" (Kass, I., and Horovitz, A., Proteins 48, 611-617, 2002) greater than or equal to 0.5. In some configurations, the methods can comprise identifying hubs having a rank order in the $40^{th}$ percentile or greater of the hubs comprising the network.

In yet other aspects, the present teachings set forth methods for designing a therapeutic agent. In various configurations, these methods comprise: (a) identifying one or more hub residue positions by the methods set forth herein; (b) providing, on a digital computer, one or more polypeptide sequences comprised by the biological system, wherein the one or more polypeptide sequences comprise the one or more hub residue positions; and (c) designing a molecule which is predicted to bind to at least one hub residue position using software comprised by the digital computer. In some configurations, these methods can further comprise designing a molecule which is predicted to interfere with at least one interaction between a hub residue position and at least one amino acid position covarying with the hub residue position. In addition, in various aspects of these teachings, a pharmaceutical agent can be a macromolecule such as an antibody, a peptide, or an organic compound of molecular weight of from about 60 Da up to about 2000 Da. In various configurations, an organic molecule can have a molecular weight of from about 100 Da up to about 1500 Da, or from about 200 Da up to about 1000 Da.

In various configurations of these aspects, a hub residue can have a rank order in the $50^{th}$ percentile or greater of the hubs comprising a network; a rank order in the $60^{th}$ percentile or greater of the hubs comprising a network; a rank order in the $70^{th}$ percentile or greater of the hubs comprising a network; a rank order in the $80^{th}$ percentile or greater of the hubs comprising a network; or a rank order in the $90^{th}$ percentile or greater of the hubs comprising a network, wherein the rank order is determined by the number of edges extending to a hub. In addition, in various configurations, a hub amino acid residue, which is defined herein as node having at least 5 edges with other amino acid residues (nodes), can be a hub having at least 6 edges, a hub having at least 7 edges, a hub having at least 8 edges, a hub having at least 9 edges, a hub having at least 10 edges, a hub having at least 40 edges, a hub having at least 50 edges, or a hub having at least 60 edges.

In various aspects of the present teachings, a biological system to which the methods can be applied can be, without limitation, an infectious agent such as a virus. In some configurations, a virus can be a DNA virus or an RNA virus. Without limitation, an RNA virus can be a single stranded RNA virus, such as a single stranded RNA positive-strand virus, or a single stranded RNA negative-strand virus. In some configurations, a single stranded RNA positive-strand virus can be a single strand RNA positive-strand virus, no DNA stage, such as a flaviviridae. Without limitation, a flaviviridae can be a hepacivirus such as a Hepatitis C virus. In some configuration, a Hepatitis C virus can be of any Hepatitis C virus subtype, such as a Hepatitis C virus subtype 1a or a Hepatitis C virus subtype 1b. In some aspects, an infectious agent can be a prokaryotic microorganism such as a bacterium, including an infectious or pathogenic bacterium, or a eukaryotic microorganism such as, but not limited to, a yeast such as a *Saccharomyces cerevisiae* or a *Schizosaccharomyces pombe*. Some bacteria to which methods of the present teachings can be applied include, without limitation, *Escherichia coli* and *Salmonella typhimurium*. In addition, in some aspects of the present teachings, the methods described by the inventors can be applied to macroscopic organisms, including plants and animals. In some configurations, a plant can be an *Arabidopsis thaliana*, and an animal can be from any phylum, including, but not limited to, vertebrates, insects, and nematodes. Vertebrates can include fish such as a zebrafish (*Brachydanio rerio*), amphibians, reptiles, birds and mammals. Mammals to which the disclosed methods can be applied include, without limitation, humans and rodents such as rats and mice. Insects to which the disclosed methods can be applied include, without limitation, *Drosophila melangaster*. Nematodes to which the disclosed methods can be applied include, without limitation, *Caenorhabditis elegans*.

In aspects of the present teachings that provide for methods of selecting a therapy, a selected therapy can be, without limitation, an interferon-based therapy, a guanosine analog-based therapy, or a combination thereof.

In some aspects of the present teachings, the inventors disclose methods of establishing a differential diagnosis for an infectious disorder. In various configurations, these methods comprise: determining amino acids occupying a plurality of diagnostic amino acid residue positions comprised by one or more polypeptides encoded by an infectious agent infecting a subject; and assigning the infectious agent infecting the subject to a covariance network selected from a plurality of covariance networks, each network comprising a unique rank order of hubs, whereby the diagnosis is selected on the basis of the covariance network assignment. In various configurations, these methods can further comprise identifying the plurality of covariance networks, wherein the identifying comprises: (i) determining an amino acid sequence of one or more polypeptides of each isolate of a plurality of isolates of an infectious agent; (ii) identifying covariance pairs of amino acid residues; and (iii) identifying a plurality of hubs, thereby establishing a plurality of networks in which each network comprises a unique rank order of hubs. Furthermore, a plurality of covariance networks can comprise at least a first covariance network and a second covariance network, and, in some configurations, at least one hub can be comprised by the first covariance network but not comprised by the second covariance network.

DETAILED DESCRIPTION

Figure 1:
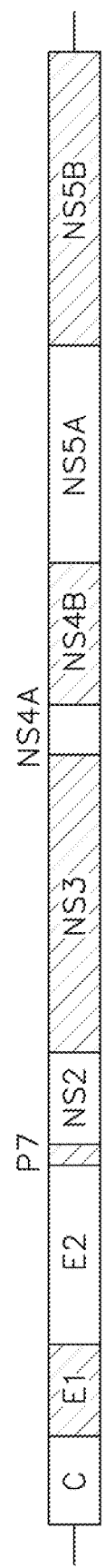
FIG. 1: The HCV genome: The ~9,600 nt long positive-polarity HCV RNA genome contains 5' and 3' untranslated regions (UTR's) and a single open reading frame that is translated into a ~3010 amino acid polyprotein. The polyprotein is cleaved to ten mature viral proteins: C, the capsid protein; E1 and E2, the envelope glycoproteins; P7, a putative ion channel; NS2, a protease; NS3, a protease and helicase; NS4A, a cofactor for NS3; NS4B, the putative organizer of the viral replicase complex; NS5A, a multifunctional regulatory protein; NS5B, the RNA polymerase.

The present inventors have developed new analytical tools for predicting intramolecular and intermolecular interactions among proteins. The present inventors have furthermore applied these analytical tools to reveal interactions within biological systems which have hitherto been unknown. Without being limited by theory, the inventors believe that in a biological system, covariance exhibited by amino acid residue positions indicates functional interactions between those positions. As used herein, a "biological system" can be any reproducing biological entity, such as a virus, a bacterium, a eukaryotic microorganism an animal, or a plant, or any symbiotic system, including commensal and parasitic systems. In a biological system, the amino acid residue positions exhibiting covariance within a biological system can be related in a network. The elements of the network—the nodes and edges—reveal "hub" amino acid residue positions, wherein each hub exhibits covariance with multiple other amino acid residue positions. As used herein, a hub residue position is a node with 5 or more edges, i.e., a hub amino acid residue position exhibits covariance with at least 5 other amino acid residue positions. Without being limited by theory, the inventors believe that such hub residue positions are positions which can play important roles in the biochemistry of a biological system. Furthermore, without being limited by theory, the biological or biochemical significance of a hub is believed to increase with increasing number of covarying amino acid residue positions ("spokes"). Hence, identification of hubs in a biological system provides a novel approach for diagnosis and prognosis, and for developing new therapies and therapeutic agents.

Hence, in some aspects of the present teachings, the inventors provide methods of identifying one or more targets for designing a therapeutic agent. Such methods comprise: determining an amino acid sequence of one or more polypeptides of each isolate of a plurality of isolates of a biological system; identifying covariance pairs of amino acid residues; establishing a network comprising the covariance pairs; and identifying one or more hub residue positions. As used herein, rank order is determined by comparing the number of edges among the hubs in a network; hubs with the more edges have a higher rank order. In various aspects, a hub residue position can be of biological significance and can serve as a target for designing a therapeutic agent if the hub residue position has a rank order in the $40^{th}$ percentile or greater, the $50^{th}$ percentile or greater, the $60^{th}$ percentile or greater, the $70^{th}$ percentile or greater, the $80^{th}$ percentile or greater, or the $90^{th}$ percentile or greater. In various alternative aspects, a hub position's biological significance and its usefulness as a drug design target can increase with increasing edges. Hence, a hub residue position can comprise a target for designing a therapeutic agent if it has at least 5 edges, at least 6 edges, at least 7 edges, at least 8 edges, at least 9 edges, at least 10 edges, at least 40 edges, at least 50 edges, or at least 60 edges. In some aspects, the most significant hubs, i.e., the best targets for designing a therapeutic agent, can be the hubs with the greatest number of nodes in a biological system.

In some aspects, methods of the present teaching include methods of identifying one or more targets for designing or for selecting an anti-viral therapy. The methods can comprise: determining an amino acid sequence of one or more viral polypeptides of each isolate of a plurality of isolates of a virus; identifying covariance pairs of amino acid residues; establishing a network comprising the covariance pairs; and identifying one or more hub residue positions. For example, the amino acid sequence of viral isolates can be determined using methods well known to skilled artisans, such as, but not limited to, sequencing a plurality of viral isolate genomes followed by conceptual translation of each genomic sequence. In some configurations, hub residue positions can be identified within the viral polypeptides, and the most significant hubs, i.e., those hubs identified by having the greatest number of edges and/or by rank order, can then be used as targets for designing an anti-viral therapy.

In yet other aspects, methods of the present teachings include methods for selecting an antiviral therapy. Various configurations of these methods include: determining amino acids occupying a plurality of diagnostic amino acid residue positions comprised by one or more polypeptides encoded by a virus infecting a subject; and assigning the virus infecting the subject to one covariance network selected from a plurality of covariance networks, each network comprising a unique rank order of hubs, whereby the therapy is selected on the basis of the covariance network assignment. From the sequence data, a plurality of covariance networks can be identified, i.e., multiple networks can be recognized on the basis of the number and identity of the hubs. Such networks can be correlated with viral properties, such as, for example, responsiveness to various treatments. A viral isolate, such as a viral isolate obtained from an infected human, can then be assigned to an established covariance network; the most effective treatment can then be selected on the basis of the network assignment. Hence, in some configurations, the multiple networks established using the analytical methods disclosed herein can include at least a first covariance network and a second covariance network. In some configurations, a hub may be present in one covariance network but not another.

In some aspects of the present teachings, similar methods can be used to select a therapy for infectious disorders. In various configurations, the methods include determining the amino acids occupying a plurality of diagnostic amino acid residue positions comprised by one or more polypeptides encoded by an infectious agent infecting a subject; and assigning the infectious agent infecting the subject to one covariance network selected from a plurality of covariance networks, each network comprising a unique rank order of hubs, whereby the therapy is selected on the basis of the covariance network assignment. In these aspects, the methods can further comprise methods for identifying the plurality of covariance networks. In various configurations, identifying the covariance networks can comprise (i) determining an amino acid sequence of one or more polypeptides of each isolate of a plurality of isolates of an infectious agent; (ii) identifying covariance pairs of amino acid residues; and (iii) identifying a plurality of hubs. By these methods, a plurality of networks can be established, in which each network comprises a unique rank order of hubs. The networks can be correlated with biological properties, such as responsiveness of the infectious agent to a therapeutic. For example, in some configurations, a plurality of covariance networks can comprise at least a first covariance network and a second covariance network, and a hub established for one network may not be present in a second network. Furthermore, the infectious agents assigned to one network can show a similar responses to a therapeutic intervention, while infectious agents assigned to a different network can show a different response. For example, at least one hub can be comprised by a first covariance network but not comprised by a second covariance network, and the presence or absence of a hub can thus be predictive of responsiveness to a particular therapeutic intervention. Thus, the presence or absence of a hub can be used diagnostically, providing a rational approach to choosing a therapeutic intervention for treating an infectious disorder.

In yet other aspects, the present teaching include methods of selecting a therapy for a biological disorder. Such a biological disorder can be, in non-limiting example, a genetic disorder. In various configurations, these methods comprise determining the amino acids occupying a plurality of diagnostic amino acid residue positions comprised by one or more polypeptides encoded by a biological system; and assigning the biological system to one covariance network selected from a plurality of covariance networks, each network comprising a unique rank order of hubs, whereby the therapy is selected on the basis of the covariance network assignment. In some configurations, these methods can include methods for identifying the plurality of covariance networks, wherein the identifying comprises: (i) determining an amino acid sequence of one or more polypeptides of each isolate of a plurality of isolates of the biological system; (ii) identifying covariance pairs of amino acid residues; and (iii) identifying a plurality of hubs, thereby establishing a plurality of networks in which each network comprises a unique rank order of hubs. In some configurations, the plurality of covariance networks can comprise at least a first covariance network and a second covariance network. In these configurations, at least one hub can be comprised by the first covariance network but not comprised by the second covariance network.

In yet other aspects, methods of the present teaching include methods of identifying functionally interacting amino acid residue positions comprised by one or more polypeptides comprised by a biological system. In various configurations, these methods comprise: determining an amino acid sequence of one or more polypeptides of each isolate of a plurality of isolates of the biological system; and identifying one or more hubs, wherein each hub comprises a plurality of covariance pairs of amino acids, whereby a covariance pair is indicative of functional interactions between the amino acids comprising the covariance pair. In some configurations, the methods can further comprise establishing a network comprising the one or more hubs. Furthermore, in some configurations, each hub can be assigned a hub a rank order within the network, wherein the rank order is determined by the number of edges for each hub. In some other configurations, the methods can comprise identifying hubs having a rank order in the $40^{th}$ percentile or greater, in the $50^{th}$ percentile or greater, in the $60^{th}$ percentile or greater, in the $70^{th}$ percentile or greater, in the $80^{th}$ percentile or greater, in the $90^{th}$ percentile or greater. In yet other configurations, the methods of identifying functionally interacting amino acid include identifying hubs having at least 5 edges, at least 6 edges, at least 7 edges, at least 8 edges, at least 9 edges, at least 10 edges, at least 20 edges, at least 30 edges, at least 40 edges, at least 50 edges, or at least 60 edges.

In some aspects of the present teachings, methods are provided for designing a therapeutic agent for a biological system. In various configurations, these methods comprise: (a) identifying one or more hub residue positions using the methods set forth herein, and (b) providing, on a digital computer, one or more polypeptide sequences comprised by the biological system, wherein the one or more polypeptide sequences comprise the one or more hub residue positions; and (c) designing a molecule which is predicted to bind to at least one hub residue position using software comprised by the digital computer. In some configurations, a therapeutic agent can be designed by combining information about a hub amino acid residue position with other information, such as coordinates specifying a three-dimensional structure of a protein comprising the hub position, as determined by x-ray crystallography and/or nuclear magnetic resonance spectroscopy. Hence, in some configurations, designing a molecule which is predicted to bind to at least one hub residue position can further comprise designing a molecule which is predicted to interfere with at least one interaction between a hub residue position and at least one amino acid position covarying with the hub residue. The interference can be positive or negative, i.e., molecular design techniques which are well known to skilled artisans can be used to develop inhibitors or enhancers of interactions between a hub residue position and an interacting node.

The inventors previously found that HCV sequences in non-responders to pegylated interferon α plus ribavirin therapy were less variable than sequences from responders to therapy in a few viral genes (Donlin, M. J., et al., J. Virol. 81, 8211-8224, 2007). The inventors interpreted this to mean that viral isolates with a relatively tight genetic distribution around an "optimum" sequence were more able to withstand the pressures induced by antiviral therapy, and those that were more genetically distant from this "optimum" were less able to survive. Here, the inventors extend this analysis by taking a systems-level approach.

The inventors found that many of the amino acid positions in the HCV open reading frame vary in concert with other positions in the genome. Genetic co-variance indicates a functional interaction between the covarying residues, but it does not identify the nature of the interaction. The functional linkages could involve direct binding between the covarying residues, compensatory allosteric changes within a protein, and/or compensatory changes on the surface of the HCV proteins needed to maintain interactions with host or other viral proteins. The inventors favor the hypothesis that most of the positions that the inventors have identified covary due to physical interactions between the viral proteins because the covarying positions are largely solvent-exposed or are within transmembrane regions that can interact with each other, but the residues forming a pair were rarely close enough in three-dimensional space for them to bind to each other. Furthermore, host proteins do not vary with the high frequency observed among the HCV sequences, so these covariance interactions probably do not reflect adaptation to host protein diversity. In most cases the inventors found that the covarying positions were predicted to be in the same or adjacent topological compartment, further indicating that the side-chains at these positions may interact with a common partner.

The presence of covarying amino acid positions between all HCV proteins indicates that there are probably direct or indirect physical interactions among all or nearly all HCV proteins. All HCV proteins are believed to form complexes either in the virion or during the biosynthetic events leading to virion formation (Moradpour, D., et al., Nat. Rev. Microbiol. 5, 453-463, 2007). In addition, complexes are formed between viral and cellular proteins during evasion of the host innate and adaptive immune responses. Our data do not address the relative contributions of these interactions to each of these processes.

Figure 5:
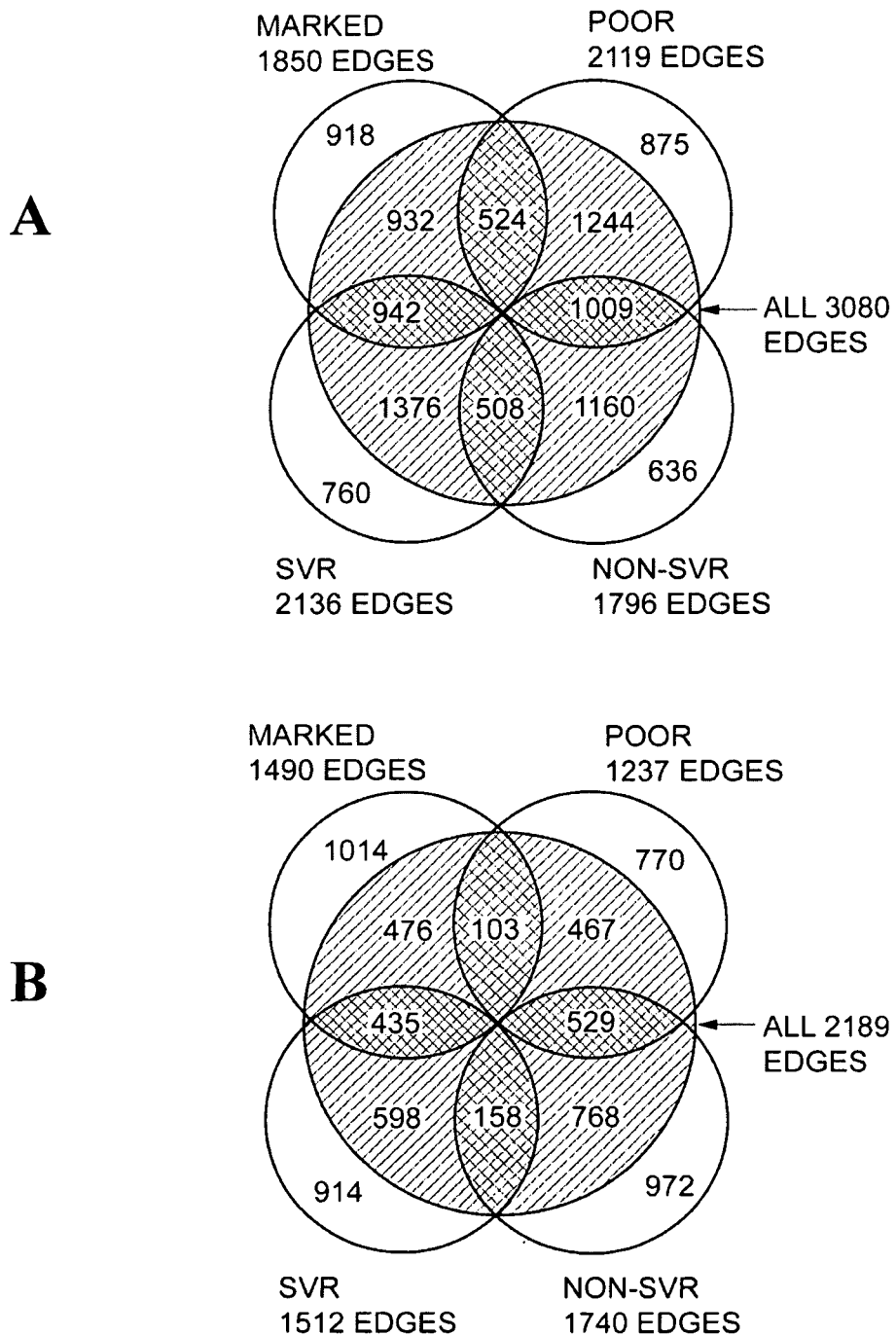
FIG. 5: Segregation of covarying pairs by phenotype: The overlap and segregation of the covarying pairs (edges) by phenotype is shown in the Venn diagram for genotype 1a (A) and genotype 1b (B). The set of covarying pairs found for all sequences are entirely contained in set of alignments found using each subset indicating that complete information for this dataset is contained within the subsets.

The inventors set forth herein a novel method of predicting a response to a therapy, and a novel method of selecting a therapy. Importantly, the inventors found that the covarying positions in the HCV genome chained together to form networks that covered all HCV proteins. The networks have a "hub-and-spoke" architecture, indicating that a few key residues covary with many other residues, but that most residues covary with only a few other positions. The covariance networks were very different between the marked and poor responders and between the SVR and non-SVR sequences. Therefore, the genetic and functional interactions implied by the covariances in the response-specific networks must represent genetic differences that affect viral response to therapy. There was a large overlap in the number of edges (covarying residue pairs) observed in the two responder classes (58% of the covarying pairs were shared between the marked and SVR networks; FIG. 5), and a similar overlap was found in the non-responder classes for both genotypes (~52% of the pairs were shared between the poor and non-SVR networks). Therefore, the viral variables reflected in these networks that affect the day 28 response to therapy are largely the same as those affecting the eventual outcome of therapy.

The covariance network generated with all HCV sequences in the Virahep-C genetic database (marked, intermediate, and poor samples) was essentially the sum of the two networks generated separately from the marked and poor sequences for both genotype 1a and 1b (FIG. 5). Almost no additional edges were found in the 1a and 1b "all" networks and about half of the edges in the responder (marked and SVR) or non-responder (poor and non-SVR) networks, and almost all edges in the responder or non-responder networks were in the "all" network. This indicates that all genetic information detectable by covariance analysis quantitatively segregated into two groups that correlated with the effect of the therapy.

A single covarying network encompassing all 10 of the HCV genes was found in each of the 10 sequence alignments analyzed (all, marked, SVR, poor, and non-SVR for each genotype 1a and 1b). The covariances were intertwined throughout the structural genes that form the virion and the nonstructural genes that synthesize the virion components and regulate cellular functions. The presence of a single network spanning the genome, coupled with the functional interaction indicated by genetic covariance, implies that there is a common mechanism acting through all of the viral proteins that affects the response to therapy. In contrast, if the covariances acted by multiple different mechanisms, the inventors would have observed two or more networks in each alignment that were either unconnected or poorly connected. The diverse functions of the viral proteins in turn implies that this common mechanism acts at three or more levels: synthesis of the viral components, assembly and/or function of the virion, and interdiction of host antiviral responses.

The mechanism by which the genetic variation reflected in the networks contributes to differential response to interferon-based therapy may have been revealed by analysis of the chemical properties of the covarying residues. HCV sequences from the non-responders (e.g., poor and non-SVR) had many more hydrophobic residues in the covarying pairs (e.g., Val, Ile, Leu, Met, Phe, Trp, Tyr, or Cys) than sequences from the responders. In contrast, the responders had many more hydrogen bond donors or acidic-basic residue pairs. Hydrophobic interactions contribute much more to protein stability in an aqueous environment than hydrophilic interactions. Therefore, our results indicate that the potential for greater stability provided by the higher hydrophobic nature of the interactions may allow some of the viruses in the population to better survive the pressures introduced by the therapy. Ribavirin has at least three proposed effects against HCV (Lau, J. Y., et al., Hepatology 35, 1002-1009, 2002), and interferon α activates a multitude of host barriers that prevent the spread of infection (Gale, M., and Foy, E. M., Nature 436, 939-945, 2005). Therefore, it is unlikely that the generalized increase in the hydrophobic nature of proteins from the viruses from non-responders acts through a few discrete intermolecular interactions. Rather, the simplest explanation is that the sum of these interactions stabilizes the virus particle to increase its infectivity and also stabilizes the replicase complex to reduce its sensitivity to the intracellular effectors of the type I interferon response. This implies that clearance of the virus during interferon-based therapy requires both lower cell-to-cell infectivity of the virions and higher sensitivity of the infected cells to interferon.

Our previous position-based analyses of these sequences revealed that HCV sequences from patients who responded well to interferon and ribavirin therapy were more variable in genes implicated in counteracting the type I interferon response (Donlin, M. J., et al., J. Virol. 81, 8211-8224, 2007). Here, the inventors found that discrete, genome-wide networks of covarying amino acids exist in sequences from responders and non-responders, and that the non-responders have many more hydrophobic amino acids in the covarying pairs than the non-responders. These new observations have four implications. First, the genetic distinction between HCV sequences from the responders and non-responders is more widespread throughout the viral genome than the inventors previously found. Second, similar numbers of covarying positions and residues were found in the non-responder and responder sequences, despite higher overall variability in the responder sequences. Therefore, there is at least one pattern to the variance in the sequences that was not previously identified. Third, the greater number of hydrophobic interactions in the non-responder networks implies that the genetic "optimum" the inventors proposed to exist in the non-responders (Donlin, M. J., et al., J. Virol. 81, 8211-8224, 2007) may be due at least in part to the greater stability of the interactions among the viral protein implied by their more hydrophobic natures.

The presence of hub-and-spoke networks in the HCV genome specific to the outcome of antiviral therapy has three medical implications. First, the non-overlapping nature of the covariances among the networks from the marked and poor response classes may provide a basis for a sequence-based diagnostic test that could reveal the susceptibility of individual HCV isolates to interferon-based therapies. Second, the residues that form the hubs in the HCV networks have a great number of functional (and possibly physical) interactions with other residues. Disrupting binding at a hub position would be predicted to weaken this web of interactions, and therefore, the HCV hub positions may be attractive antiviral drug targets. Finally, covariance network analysis should be applicable to essentially all RNA viruses due to their high genetic variability. If similar networks correlating with virulence or drug sensitivity are found in other viruses, covariance network analysis should open a wide range of analytical and therapeutic options in both medical and agricultural settings.

EXAMPLES

Various aspects of the present teachings can be illustrated by the following non-limiting examples. The following examples are illustrative, and are not intended to limit the scope of the claims. The description of a composition or a method in an example does not imply that a described article or composition has, or has not, been produced, or that a described method has, or has not, been performed, except for results presented in past tense.

The methods described herein utilize laboratory techniques well known to skilled artisans, and guidance can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A. Laboratory Manual, Cold Spring Harbor Laboratory Press, Cold Spring Harbor, N.Y., 1999, and textbooks such as Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004. Networks and network theory are discussed in references such as Barabasi, A.-L., Linked: The new science of networks, Perseus Publishing, Cambridge, Mass., 2002; Newman et al. The Structure and Dynamics of Networks, Princeton University Press, 2006; Watts, D. J., Six degrees: The science of a connected age, W. W. Norton & Company, 2003; Watts, Duncan J. Small Worlds: The Dynamics of Networks between Order and Randomness. Princeton University Press, 1999.

Sequencing: Consensus sequences for the full HCV ORF were obtained by directly sequencing overlapping nested RT-PCR amplicons as described (Yao, E., and Tavis, J. E., Virol. J. 2, 88, 2005). Briefly, HCV RNA was isolated from plasma and nested RT-PCR was performed. Both strands of the amplified DNAs were sequenced using ABI dye-terminator technology; sequence depth averaged over four-fold. Sequences were assembled using Vector NTI and base-calling errors were corrected following inspection of the chromatograms. Mixed-base positions due to the HCV quasispecies were resolved by identifying the predominant base at each position. The extreme 3' end of the ORF could not be amplified in a few samples, and hence the C-terminal 56 amino acids of NS5B were excluded from the analyses to ensure that all sequences were represented equally. The Virahep-C sequences have been deposited in Genbank (EF407-411 to EF407504).

Response classes and patient characteristics: Ninety-four viral sequences were employed in this study, stratified by genotype (1a vs. 1b) and day 28 responses to therapy (marked, intermediate, or poor); all patients received full doses of both peg-interferon and ribavirin for the first 28 days. Marked responders had a decline in HCV titres of >3.5 $\log_{10}$ or to undetectable between baseline and day 28 of therapy, intermediate patients had declines of 3.5-1.4 log, and poor responders had declines of <1.4 log. Response to therapy was defined at 28 days of therapy to separate patients with null responses to therapy from patients who had robust primary biological responses to therapy. In some analyses, the samples were stratified by eventual outcome of therapy [sustained viral response (SVR; undetectable HCV viremia six months following therapy) vs. non-SVR].

Calculation of covariance pairs: The inventors implemented and evaluated three previously published algorithms to identify covarying positions (Olmea, O., et al., J. Mol. Biol. 293, 1221-1239, 1999; Atchley, W. R., et al., Mol. Biol. Evol. 17, 164-178, 2000; Kass, I., and Horovitz, A., Proteins 48, 611-617, 2002). Algorithms that measure correlated variations must favor an intermediate level of conservation because a balance must be found between false positives at non-conserved positions (where a random frequency of amino acids is observed), and false negatives (from positions where residues are completely conserved). The HCV genome contains many positions that are completely conserved, with islands of variable positions. Based on empirical evidence that was in accord with the results of Fodor and Aldrich (Fodor, A. A., and Aldrich, R. W., Proteins 56, 211-221, 2004), the inventors found that the observed minus expected square (OMES) method (Kass, I., and Horovitz, A., Proteins 48, 611-617, 2002) performed well on this dataset. The alignments for each subset were generated using Clustal W (Jeanmougin, F., et al., Trends Biochem. Sci. 23, 403-405, 1998) as previously described (Donlin, M. J., et al., J. Virol. 81, 8211-8224, 2007).

To identify the covarying pairs, the inventors calculated for every possible pair of columns i and j, a score S using observed and expected pairs:

$$S = \frac{\sum_{1}^{L}(N_{OBS} - N_{EXP})^2}{N_{valid}}$$

where L is the list of all observed pairs and $N_{obs}$ is the number of occurrences for a pair of residues. The expected number for the pair is given by:

$$N_{EXP} = \frac{C_{xi}C_{yj}}{N_{valid}}$$

in which $N_{valid}$ is the number of sequences in the alignment that are non-gap residues, $C_{xi}$ is the observed number of residue x at position i, and $C_{yj}$ is the observed number of residues y at position j. The expected number of column pairs calculated in this manner provides a reasonable null model for comparisons of the observed pairs. An OMES score of 0.5 was used as the cutoff for all analyses.

Calculation of solvent exposure: The solvent exposure was calculated using the method of Lee and Richards (Lee, B., and Richards, F. M., J. Mol. Biol. 55, 379-400, 1971) as implemented in a FORTRAN program described previously (Aurora, R., et al., Science 264, 1126-1130, 1994). The raw exposed surface area was normalized using the tripeptide as a standard state (Lesser, G. J., Rose, G. D., Proteins 8, 6-13, 1990). The normalized exposure was averaged over all side-chain atoms, and the residue was considered to be solvent exposed if it had greater than 40% exposed side-chain atoms.

Topology and structural analyses: First, the transmembrane regions were predicted using TMHMM (Kahsay, R. Y., et al., Bioinformatics 21, 1853-1858, 2005; von Sonnhammer, E. L., et al., Proc. Int. Conf. Intell. Syst. Mol. Biol. 6, 175-182, 1998). Next, these regions were then mapped on to the positions of signal sequences and combined with the location of proteins (e.g., cytoplasm, ER lumen, or transmembrane) from the published literature (Penin, F., Clin. Liver Dis. 7, 1-21, vii, 2003; Reed, K. E., and Rice, C. M., Curr. Topics Microbiol. Immunol. 242, 55-84, 2000). Intra-residue distances were calculated using the PDB coordinates as inputs using a program custom written for this purpose. RASMOL version 2.7 (Sayle, R. A., and Milner-White, E. J., 1995. Trends Biochem. Sci. 20, 374, 1995) was used to calculate distances for specific position pairs in monomers.

Computational Analyses: The program to calculate covariance scores and ancillary analyses was written in Python. All statistical tests were performed using R(R Development Core Team, 2004, The R Foundation for Statistical Computing, Vienna, 2004). Example 1 This example illustrates Virahep-C sequences.

The consensus sequence for the full-length HCV open reading frame was previously determined from 94 participants in the Virahep-C clinical study (Donlin, M. J., et al., J. Virol. 81, 8211-8224, 2007). The characteristics of these patients have been described previously and are summarized in Table 1. These patients were evenly stratified by HCV genotype (1a vs. 1b) and day 28 response to therapy (marked, >3.5 log decline in viral titre or to undetectable; intermediate, 3.5-1.4 log decline; or poor, <1.4 log decline). To focus on the extremes of response to therapy, the inventors employed just the 63 marked and poor sequences for many analyses reported here (16 1a marked, 15 1b marked, 16 1a poor, and 16 1b poor). The Virahep-C genetics study stratified these sequence by the day 28 responses to eliminate non-biological effects on changes in viral titre (such as poor drug compliance). However, the success of treatment (SVR or non-SVR) was known for these patients, and so in some covariance analyses the sequences were also stratified by treatment outcome.

TABLE 1

Baseline characteristics of patients in the Virahep-C genetics study.

| Parameter | Statistic | Marked | Poor | P |
|---|---|---|---|---|
| Number of Patients | N | 31 | 32 | |
| Age (Years) | Mean ± std. dev. | 46.5 ± 6.2 | 49.4 ± 8.8 | 0.30[1] |
| Male | N (%) | 22 (71%) | 21 (65.6%) | 0.40[2] |
| Body Weight (kg) | Mean ± std. dev. | 84.9 ± 16.8 | 91.0 ± 13.5 | 0.28[2] |
| African-Americans | N (%) | 16 (51.6%) | 16 (51.6%) | 0.9[4] |
| HCV RNA ($\log_{10 IU/ml}$) | Mean ± std. dev. | 5.9 ± 0.9 | 6.4 ± 0.5 | 0.003[3] |
| Alanine aminotransferase (U/L) | Mean ± std. dev. | 79.0 ± 52.3 | 86.3 ± 43.6 | 0.17[3] |
| Albumin (g/dl) | Mean ± std. dev. | 4.1 ± 0.4 | 4.2 ± 0.3 | 0.29[3] |
| Ishak necroinflammation score (0-18) | Mean ± std. dev. | 7.2 ± 2.5 | 7.9 ± 2.7 | 0.52[3] |
| Ishak fibrosis score (0-6) | Mean ± std. dev. | 1.8 ± 1.3 | 2.3 ± 1.4 | 0.15[3] |

[1] Chi-square
[2] Analysis of variance
[3] Kruskal-Wallis; missing = 1

Example 2

This example illustrates identification of covarying amino acid positions in the HCV genome. To identify covarying amino acid positions in the HCV open reading frame, the inventors began by creating ten multiple sequence alignments: 1a-all, 1a-marked, 1a-poor, 1a-SVR, 1a-non-SVR, 1b-all, 1b-marked, 1b-poor, 1b-SVR, and 1b-non-SVR. A covariance score for every possible pair of positions in each alignment was calculated by squaring the difference between the number of observed and expected amino acid pairs and normalizing this difference by the number of entries (excluding gaps) in each column (OMES method) (Kass, I., and Horovitz, A., Proteins 48, 611-617, 2002). The null model in this analysis is the expected number of covarying pairs, which is based on the count of each amino acid at each of the two positions of each pair of positions. Therefore, two perfectly conserved columns will have a score of zero because the expected and observed numbers are equal. Covarying positions were defined as those pairs with scores ≥0.5. This corresponds to a difference of at least 3 observed covarying pairs between the observed and expected. While this choice was arbitrary, it provided a reasonable number of comparisons across the phenotype classes. In addition, during analyses of shuffled alignments, the inventors observed maximum sensitivity using a cutoff of 0.5. Examples of Hepatitis C virus sequences including polyprotein sequences can be found in U.S. Provisional Patent Application 60/945,543, filed Jun. 21, 2007, the specification of which is herein incorporated by reference in its entirety.

There were 301 covarying positions in genotype 1a and 280 in genotype 1b, representing about 10% of the 2955 columns in the alignment for each genotype. The covarying positions were spread throughout the genome, with positions in each of the 10 viral genes covarying with positions in all of the other nine genes. All but one of these covarying positions (position 1583) are different than the known adaptive mutations required for efficient HCV RNA replication in the replicon culture system (Blight, K. J., J. Virol. 81, 5724-5736, 2007; Dustin, L. B., and Rice, C. M., Ann. Rev. Immunol. 25, 71-99, 2007).

The difference between the number of covarying positions in the marked and poor responders (202 vs. 172 for 1a and 255 vs. 195 for 1b, respectively) was not significant for either genotype by the Fisher's exact test. Similarly, no significant differences in the number of covarying positions were found when the same sequences were analyzed by treatment outcome (223 SVR vs. 217 non-SVR for 1a, 262 SVR vs. 221 non-SVR for 1b). Therefore, while covarying positions were common and wide-spread in the HCV genome, there were no significant differences in the numbers of covarying positions between the treatment response classes.

Example 3

This example illustrates that covarying positions form networks. Closer inspection of the covarying positions in the alignments revealed that one member of a covarying pair often covaried with one or more other positions in the genome. This led us to hypothesize that the covarying positions may be linked together into a network. To test this hypothesis, the inventors represented the covarying pairs as graphs. A graph is a collection of nodes (here, amino acid positions) connected by edges (represented as lines) if they display covariance.

Figure 2A:
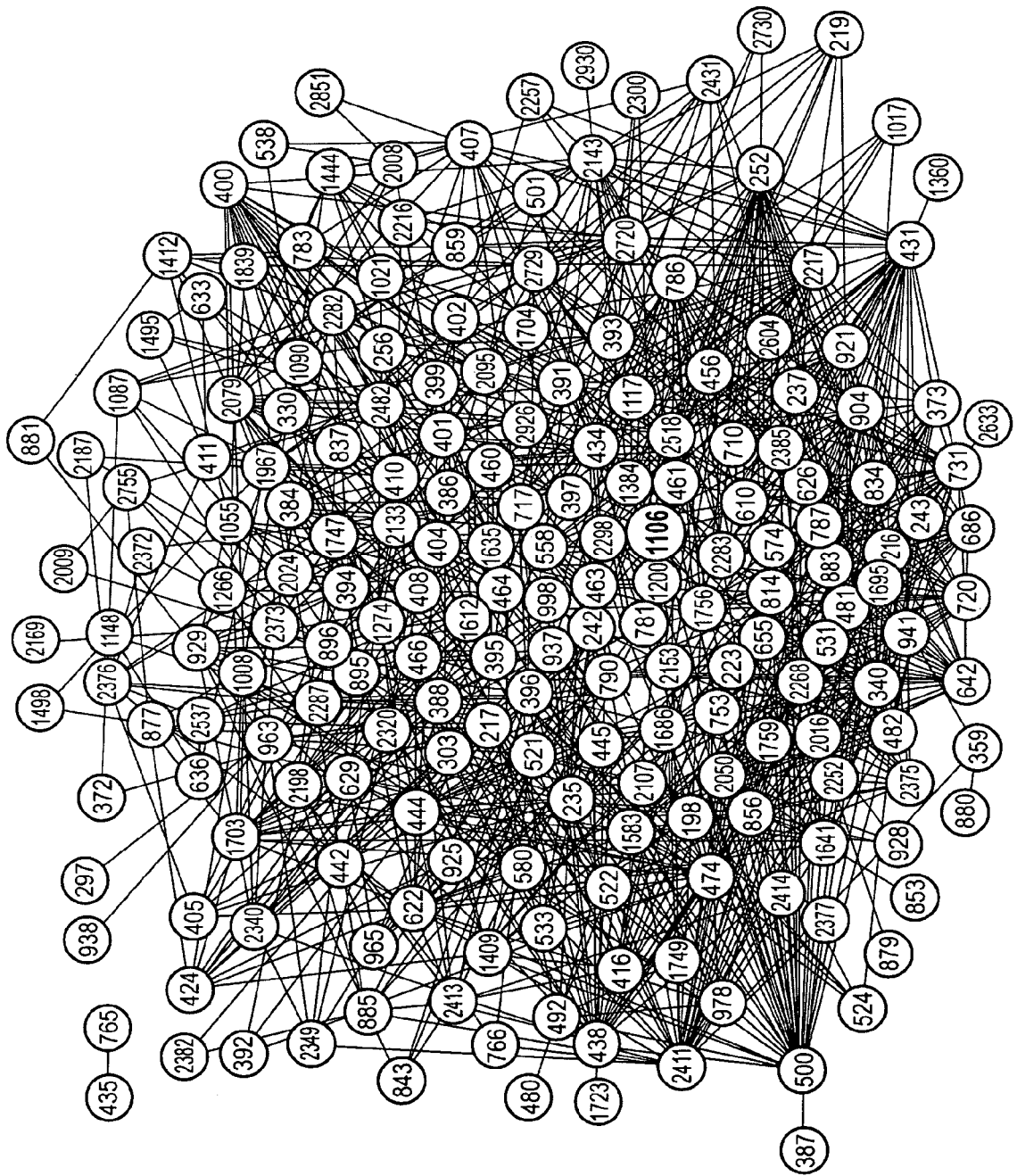
FIG. 2: High-resolution covariance networks: The covariant pairs of columns identified from marked (panel A) and poor (panel B) responders are shown for genotype 1a. Position 1106 in panel A and position 2050 in panel B represent the highest connected hub nodes in each network.
Figure 2B:
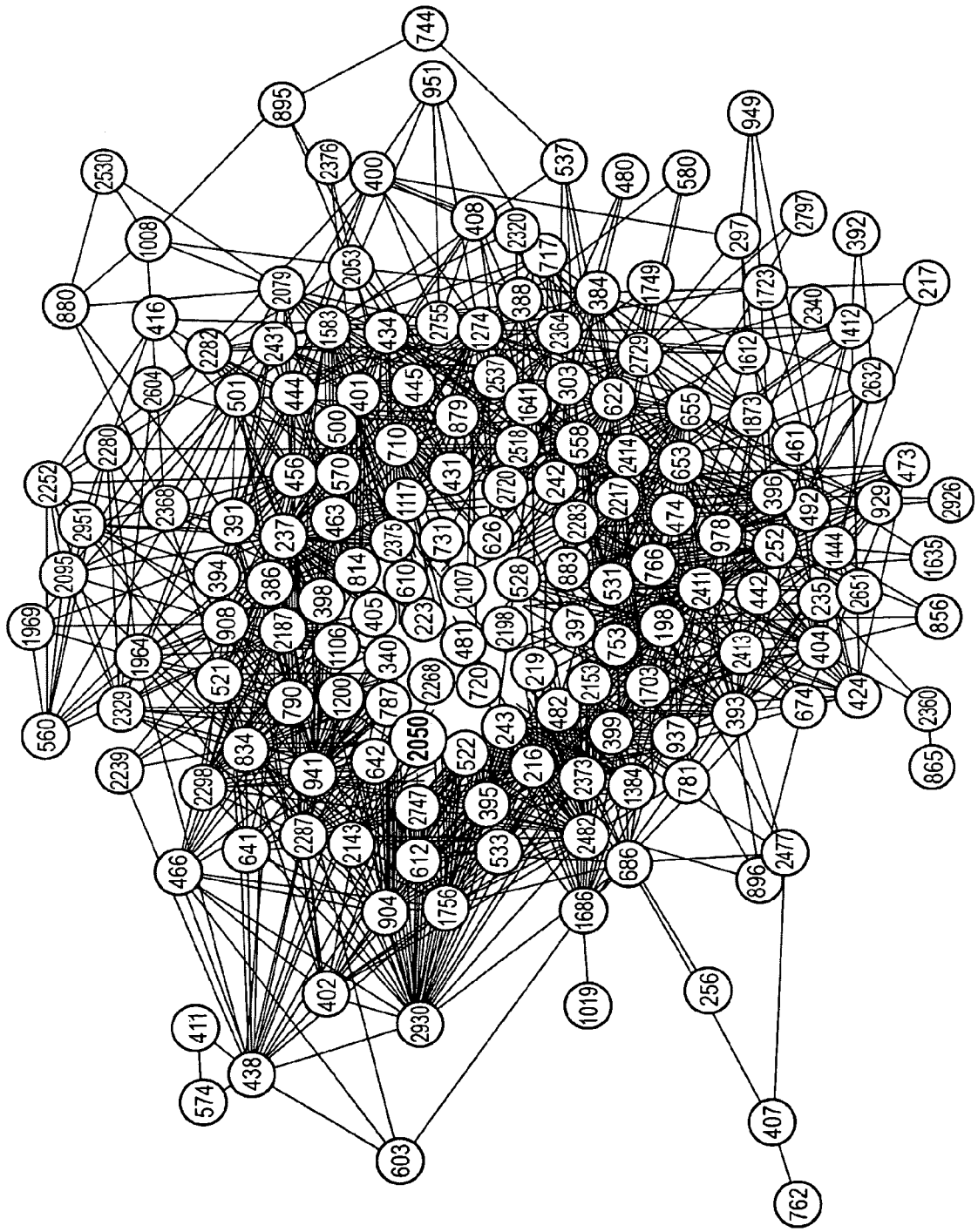
Figure 3A:
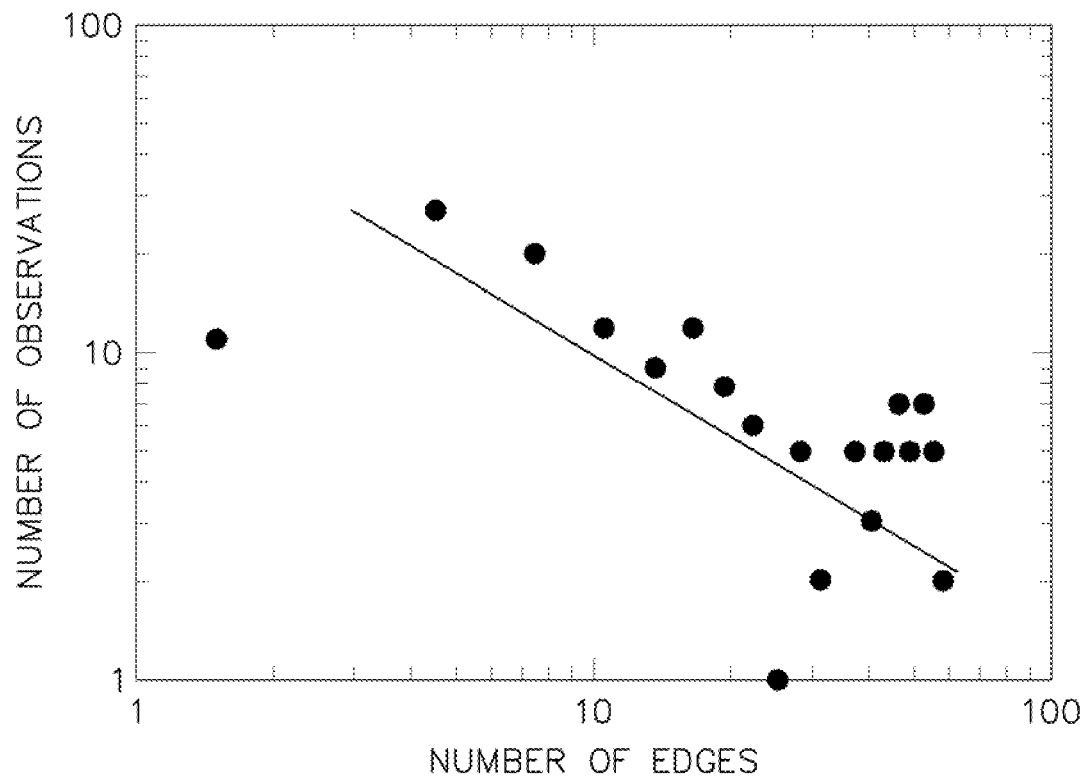
FIG. 3. Hub-and-spoke nature of the networks: The log-transformed number of nodes with a given number of edges per node (k) was plotted against the log of frequency (i.e., log(Pr)=−γ log(k)) for genotype 1a marked (panel A; γ~1.2) and poor responders (panel B; γ~1.0). The plots show that the graphs follow the inverse power-law distribution, and these values of γ indicate that these networks have a hub-and-spoke architecture.
Figure 3B:
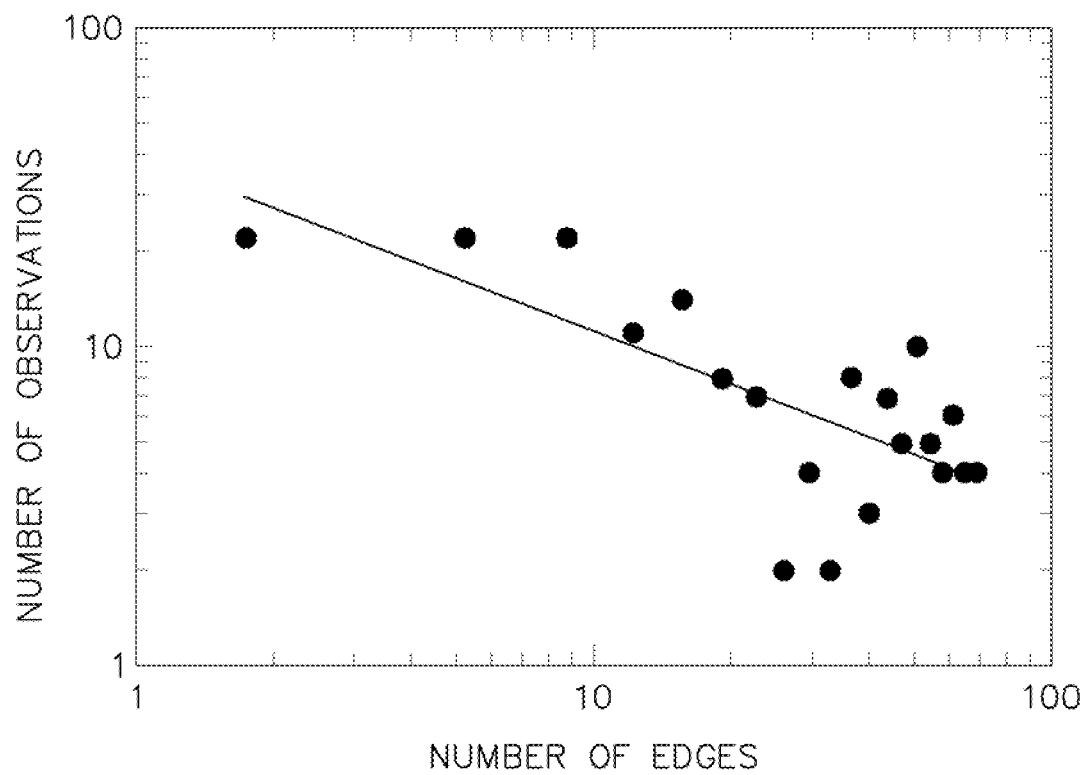

Graphs were generated for the covarying positions in each of the response classes and rendered using Cytoscape (Shannon, P., et al., Genome Res. 13, 2498-2504, 2003) (FIGS. 2A and 2B). The graphs revealed that the covarying positions do indeed form networks because the covarying positions formed chains of interconnected residues. The networks all followed the inverse power law distribution, where the probability that any node has k edges is given by: $Pr(k)=k^{-\gamma}$ (Barabasi, A.-L., Linked: The new science of networks, Perseus Publishing, Cambridge, Mass., 2002; Albert & Barabasi, Phys. Rev. Lett. 85, 5234-5237, 2000) (FIGS. 3A and 3B). For the response class networks, $\gamma$ ranged from ~1.0 to 1.2, indicating that the networks have a "hub-and-spoke" architecture, with a few nodes (e.g., positions in the alignments) covarying with many others, but most nodes being connected to only few others. The nodes that were most highly connected (the "hubs") had covariance scores at or near the maximal value possible for alignments of this size.

Example 4

This example illustrates that covariance networks differ by response classes. The characteristics for the networks generated from each of the 10 alignments are shown in Table 2.

TABLE 2

| Network characteristics | | |
|---|---|---|
| Genotype/Phenotype | Nodes[1] | Edges[2] |
| 1a All | 301 | 5277 |
| 1a Marked | 202 | 1848 |
| 1a Poor | 172 | 2118 |
| 1a SVR | 223 | 2133 |
| 1a non-SVR | 217 | 2196 |
| 1b All | 280 | 2188 |
| 1b Marked | 255 | 1490 |
| 1b Poor | 195 | 1232 |
| 1b SVR | 262 | 1512 |
| 1b non-SVR | 221 | 1740 |

[1]Nodes are the positions in the sequence alignments that covary.
[2]Edges are the amino acid pairs that covary. Each node may have multiple edges.

Overall, the numbers of nodes (covarying positions) and edges (covariances between amino acids at these positions) were similar between response classes. However, when the inventors compare the graphs from marked and poor responders and from the SVR and non-SVR sequences the inventors found that the pairs of positions forming the respective networks were different, with only a few edges shared between them (Table 3). The hubs were also very different between the response classes (Table 4). For example, for genotype 1a the positions that were most highly interconnected were within NS2, NS4A and E2 in the marked responders, but in p7, E2 and NS5A for the poor responders. In genotype 1b, the hubs in the marked responders were in NS5A, NS2, in contrast to E2 and NS2 in the poor responders. Therefore, although networks with similar numbers of covarying amino acid positions were found in all response classes, the residues and amino acid positions that form the networks differed between the response classes.

TABLE 3

| Segregation of edges by Phenotype | | | |
|---|---|---|---|
| Genotype | Responders[1] | Intersection | Non-Responders[2] |
| 1a Day 28 response | 1848 | 492 | 2118 |
| 1a Sustained response | 2133 | 464 | 1796 |
| 1b Day 28 response | 1490 | 91 | 1231 |
| 1b Sustained response | 1512 | 149 | 1740 |

[1]Marked or SVR
[2]Poor or non-SVR

TABLE 4

The top 5 most connected nodes by class

| Node | Edges | Protein | Node | Edges | Protein | Node | Edges | Protein |
|---|---|---|---|---|---|---|---|---|
| 1a All | | | 1a Marked | | | 1a Poor | | |
| 242 | 89 | E1 | 883 | 57 | NS2 | 753 | 70 | p7 |
| 482 | 83 | E2 | 1686 | 57 | NS4A | 610 | 70 | E2 |
| 753 | 82 | p7 | 904 | 56 | NS2 | 2050 | 69 | NS5A |
| 610 | 82 | E2 | 655 | 56 | E2 | 626 | 68 | E2 |
| 710 | 81 | E2 | 481 | 56 | E2 | 482 | 68 | E2 |
| 1b All | | | 1b Marked | | | 1b Poor | | |
| 891 | 62 | NS2 | 2257 | 38 | NS5A | 524 | 31 | E2 |
| 887 | 51 | NS2 | 856 | 37 | NS2 | 891 | 29 | NS2 |
| 1496 | 50 | NS3 | 2143 | 36 | NS5A | 768 | 29 | p7 |
| 720 | 48 | E2 | 887 | 34 | NS2 | 407 | 29 | E2 |
| 479 | 48 | E2 | 916 | 32 | NS2 | 1011 | 29 | NS2 |

| Node | Edges | Protein | Node | Edges | Protein |
|---|---|---|---|---|---|
| 1a SVR | | | 1a non-SVR | | |
| 216 | 66 | E1 | 610 | 61 | E2 |
| 481 | 65 | E2 | 242 | 57 | E1 |
| 1756 | 65 | NS4b | 1200 | 57 | NS3 |
| 814 | 64 | NS2 | 463 | 56 | E2 |
| 753 | 63 | p7 | 710 | 52 | E2 |
| 1b SVR | | | 1b non-SVR | | |
| 880 | 35 | NS2 | 720 | 45 | E2 |
| 434 | 35 | E2 | 8741 | 44 | E2 |
| 608 | 33 | E2 | 2543 | 42 | NS5b |
| 2009 | 33 | NS5A | 480 | 41 | E2 |
| 2169 | 32 | NS5A | 466 | 40 | E2 |

Example 5

Figure 4:
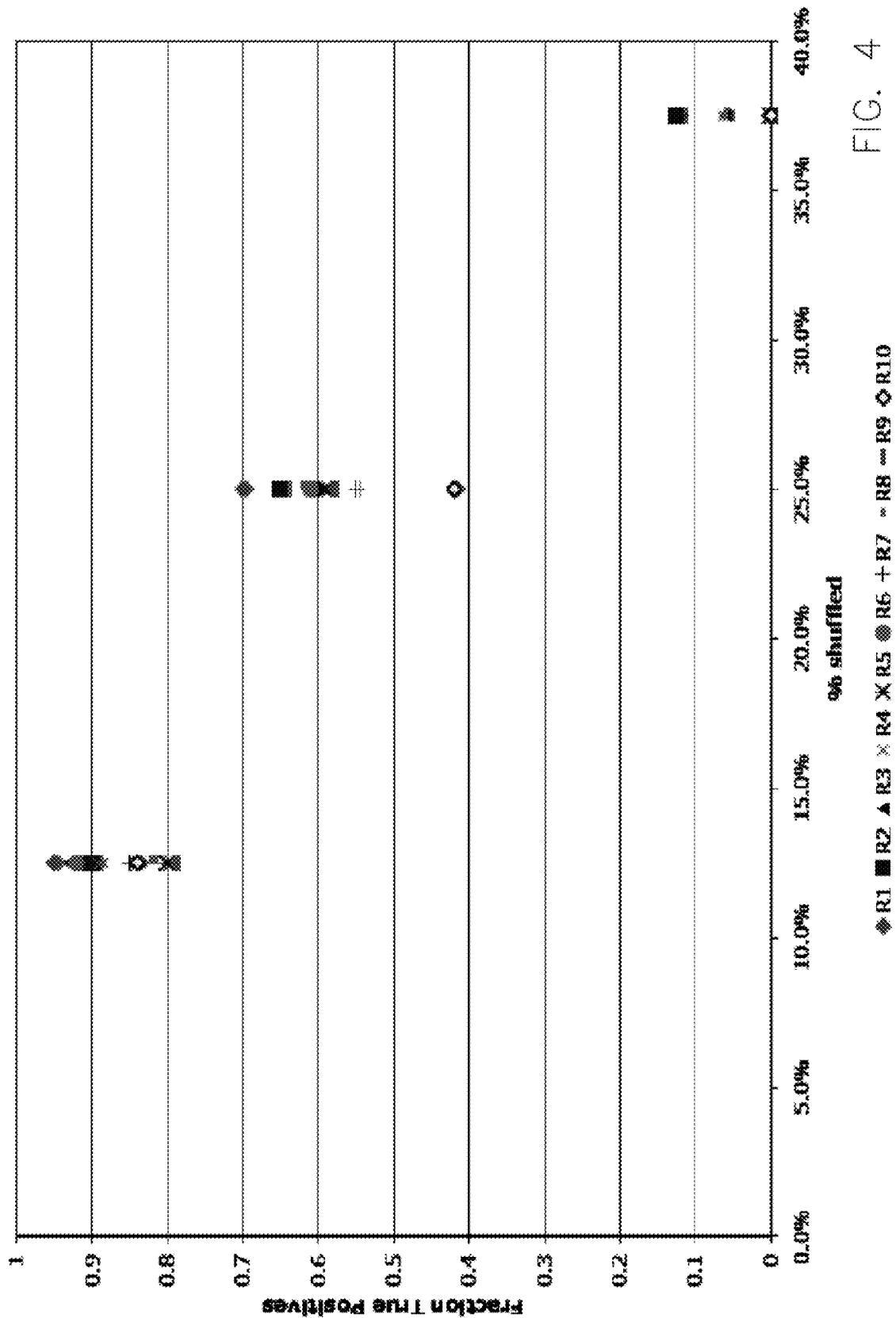
FIG. 4: Random shuffling of genotypes causes loss of information: Ten independent alignments (R1 through R10) in which sequences of the genotype 1a marked group were randomly replaced with sequences from the 1a poor group were generated at three different levels of replacement: two (12.5%), four (25%) or 6 (37.5%) of the 16 sequences. The plot shows the proportion of true positive covarying pairs relative to the unshuffled marked sequences.

This example illustrates validation of covarying pairs. To test the possibility that the differences in the marked and poor networks may have been generated by chance, the inventors generated alignments in which the inventors randomly exchanged sequences between the marked and poor responders. Alignments were generated and the covariance analysis was repeated for ten iterations at three levels of randomly exchanged sequences, 12.5% (2 HCV genomes out of 16), 25% (4 genomes), and 37.5% (6 genomes). A typical example is shown in FIG. 4 for genotype 1a marked responders shuffled with poor responders. Exchanging two sequences in the shuffled networks led to the loss of 15% of the nodes and edges (e.g., the residue positions and their interactions) identified in the un-shuffled alignments. At four changes, the number of edges decreased further, and when six sequences were shuffled the network collapsed. In every case, the pairs of positions that were identified in the shuffled alignments were also found in the "all" alignment for the same genotype. These control analyses indicate that the covariance pairs identified for the response classes were not generated by random chance, and hence that they reflect a feature of the viruses infecting the patients in the various response classes. The inventors acknowledge that the dataset used here is relatively small; nonetheless, it represents the largest coherent dataset that currently exists for such analyses.

HCV replicates as a quasispecies, but our analysis was performed on the viral consensus sequences (the most-common residue at each position) in each individual, and this intra-patient variation could affect the existence of the network. However, the control analyses in FIG. 4 indicate that the existence of these networks was tolerant of random replacement of at least 25% of the sequences with others that vary by over 10% at the amino acid level. The quasispecies variation within an individual is typically 14% at the amino acid level, and hence the networks appear to be tolerant of substitution levels considerably larger than the degree of quasispecies variability typical within a given individual.

In the initial analysis of the Virahep-C viral sequences, the inventors found that genetic diversity was highest in the marked responders, intermediate in the intermediate responders, and lowest in the poor responders (Donlin, M. J., et al., J. Virol. 81, 8211-8224, 2007). If a similar relationship exists among the covarying networks, the sum of the covariances in the marked and poor networks should contain nearly all of the covariances present when the intermediates are included in the "all" alignment. Therefore, the networks generated from alignments of all 47 1a or 1b sequences were compared to the separate networks for the marked and poor classes for the same genotype. As predicted, the "all" network contained essentially all the covariances in the marked and poor networks, and importantly, no additional edges were identified (FIG. 5). This indicates that the information contained in the all network is contained within the subsets segregated by treatment phenotype, and that no information is lost and no new interactions are identified by random chance in the full data set.

Example 6

This example illustrates that the day 28 poor and non-SVR networks have more hydrophobic pairs. To further analyze the nature of the functional interaction between the covarying residues, the inventors asked if there were differences in the chemical nature of the covarying amino acid pairs within the networks. A count of the hydrophobic amino acids in the covarying pairs revealed that in both genotypes, hydrophobic amino acid pairs (i.e., Ile-Leu or Phe-Leu) were observed significantly more often in the poor responders than in the marked responders (3.4-fold in 1a and 3.2-fold in 1b) (Table 5).

TABLE 5

Hydrophobic amino acid pairs in the covariance networks

| Genotype | Poor | Marked | Total pairs | P value[1] |
|---|---|---|---|---|
| 1a | 2401 | 706 | 6530 | $3 \times 10^{-9}$ |
| 1b | 1846 | 537 | 5152 | $2 \times 10^{-16}$ |

[1]Fisher's exact.

To determine if this high frequency of hydrophobic amino acids was a feature of the pairs of residues in the poor networks, or if it simply resulted from a higher frequency of hydrophobic amino acids in the poor responders, the inventors compared the frequency of hydrophobic amino acids in the complete marked and poor sequences and in the amino acid variations were unique to either the marked or poor response classes. There was no significant difference in the number of hydrophobic amino acids in either the total or unique analyses for either genotype. Therefore, the high frequency of hydrophobic amino acids is a property of the covarying amino acids in the networks, not a feature of the sequences as a whole. The high prevalence of hydrophobic amino acid pairs among the covarying residues in the poor responders implies that additional hydrophobic interactions resulting from these hydrophobic amino acids may have stabilized the viral proteins or their inter-molecular interactions, and this appears to somehow contributed to the survival of the virus in the face of the pressures induced by therapy.

Example 7

This example illustrates topological assessment of the covarying positions. Genetic covariance indicates a functional interaction between the covarying residues, and hence our results indicate that there are functional interactions between all 10 proteins encoded in the HCV open reading frame. Covariance interactions often reflect direct binding between the residues, but other interactions such as compensatory allosteric changes, are also common. HCV protein translation and replication take place in association with a membranous web believed to derive from the endoplasmic reticulum (Dustin, L. B., and Rice, C. M., Ann. Rev. Immunol. 25, 71-99, 2007), and most if not all of HCV's proteins are membrane-associated. Therefore, to evaluate whether the covarying residues could possibly interact directly with each other, the inventors evaluated their topological orientation relative to the cellular membranes, using either the experimentally known orientations or the inferred orientations for those residues lacking experimental data (Lindenbach, B. D., and Rice, C. M., Nature 436, 933-938, 2005). In genotype 1a the inventors found that for the 714 residue pairs that occur within the same protein, 672 were in the same compartment, 41 were in adjacent compartments (e.g., cytosol and transmembrane) and only 1 pair was in non-adjacent compartments (e.g., lumen and cytosol). For genotype 1b there were 460 pairs in the same compartment, 38 in adjacent compartments, and 10 in non-adjacent compartments among the 508 covarying pairs in the same protein. In both genotypes, there were an unexpectedly large number of covarying pairs within known or predicted transmembrane regions (58 out of 714 pairs for 1a; 42 of 508 pairs for 1b). When this analysis was expanded to include all interactions in the networks rather that restricting the pairs to the same protein, the inventors found that nearly 75% of the pairs occurred in the same or adjacent compartments for both genotypes. This indicates that many of these covarying pairs could be in direct contact with each other and/or interact with a common partner.

Example 8

This example illustrates structural assessment of covarying positions. The prediction that some of the covarying residues contact each other can be directly tested for all or part of NS2, NS3, NS5A, and NS5B because crystal structures are available for these proteins (e.g., PDB identifiers 2HD0, 1CU1, 1ZH1, and 2GIR, respectively). To this end, the inventors mapped the covariant pairs within these proteins onto the available crystal structures. An assumption of this approach is that the structure of the protein variants the inventors sequenced is identical to the structure of the protein that was crystallized. This is a reasonable first order assumption as the variant proteins are ~90% identical with the protein that was crystallized. In most cases (78%), the covarying positions were on the solvent-exposed face of the protein, but only a minority of the covarying residues (30%) were near enough to each other to potentially be in direct contact (≤7.5 Å). Therefore, most of the functional interactions identified by genetic covariance may contribute to binding interactions on the surface of the proteins, but relatively few of them appear to involve direct binding between the covarying residues.

The preceding analysis could be influenced by packing of the protein monomers in the crystal unit cells because NS3, NS5A, and NS5B all have 2 monomers/unit cell, and NS2 has eight monomers per subunit and two subunits per unit cell. Therefore, the inventors also mapped the residues on the surface of representative monomeric structures for each protein. NS2 is a transmembrane protein, but its crystal structure does not include the transmembrane regions (Lorenz, I. C., et al., Nature 442, 831-835, 2006). There were 117 intra-protein covarying pairs in genotype 1a NS2, and of these 39 covarying pairs were within the crystal structure. In 29 of these cases, the covarying pairs were on solvent-accessible surface, with no observable interactions between the residues of the pair. NS3 is a bifunctional protein with helicase and protease activity. There were 26 covariant pairs wholly within NS3 for genotype 1a, and 32 for genotype 1b. All of the pairs were on solvent exposed surfaces, but none were within 7.5 Å of each other. No intra-protein pairs were found within the N-terminal third of NS5A that is present in the crystal structure. NS5B is an RNA-dependent RNA polymerase that is located in the cytosol but is anchored to the membrane by its C-terminus. There were 21 pairs in genotype 1a and 67 pairs in genotype 1b that were wholly located within this protein, and all of the residue pairs were on the surface of the monomer, but again, none of the residue pairs were within 7.5 Å of each other.

Therefore, the large majority of these covariant residue pairs appear to be involved in inter-protein interactions because they are on the solvent-exposed surfaces of the proteins, but the side-chains of the covarying pairs in the large majority of the cases do not interact with each other.

Example 9

This example illustrates that the covariance networks found in the Virahep-C sequences are representative of networks derived from HCV sequences in general circulation.

In this example, a set of 118 full-length genotype 1a sequences from non-Virahep-C patients was collected from an HCV sequencing project conducted by the Broad Institute at the Massachusetts Institute of Technology (http://www-.broad.mit.edu/annotation/viral/HCV/ProjectInfo.html), and the polyprotein amino acid sequences of these nucleic acid sequences were deduced. Ten sets of 47 amino acid sequences were randomly chosen from the set of 118, and then each set was aligned and independently subjected to covariance analysis as described above. The distribution of the covariance scores in the ten random sets of 47 sequences were compared in a pairwise manner by the Kolmogrov-Smirnov test, and the P values ranged from 0.23 to 0.38 (non-significant). This indicates that the score distributions were statistically indistinguishable amongst the 10 permuted sets. The distribution of covariance scores in the Virahep-C genotype 1a "all" network (47 sequences) was then compared to the distribution in each of the 10 random permutations. These P values ranged from 0.23 to 0.32, with an average P value of 0.30 (non-significant). Therefore, the distribution of covariance scores within the Virahep-C data set was very similar to the distributions in non-Virahep-C data sets of equivalent size. Finally, the number of nodes, the number of edges, and the edge density were all similar, and the top 4 hub nodes were the same for all 11 sequence sets. Therefore, the covariances found in the Virahep-C sequences are representative of a randomly-chosen set of HCV sequences.

All publications and patent applications cited in this specification are herein incorporated by reference as if each individual publication or patent application were specifically and individually indicated to be incorporated by reference. Although the foregoing teachings have been described in some detail by way of illustration and example for purposes of clarity of understanding, it will be readily apparent to those of ordinary skill in the art in light of the teachings that certain changes and modifications may be made thereto without departing from the spirit or scope of the appended claims.

What is claimed is:

1. A method of establishing a plurality of sequence covariance networks useful to determine whether to treat a patient with an antiviral therapy, comprising:
   (i) obtaining a plurality of hepatitis C isolates, grouped by response to an antiviral therapy;
   (ii) determining the amino acid sequence of a plurality of hepatitis C polypeptides from each isolate;
   (iii) identifying covariance pairs of residues in the amino acid sequences of each group; and
   (iv) identifying a plurality of sequence covariance networks among the covariance pairs in each group, thereby establishing a plurality of sequence covariance networks in which each network comprises a unique rank order of hubs;
   (v) using the plurality of sequence covariance networks to determine whether to treat a specific hepatitis C-infected patient with the antiviral therapy.

2. A method in accordance with claim 1, wherein the plurality of sequence covariance networks consists of a first sequence covariance network and a second sequence covariance network.

3. A method in accordance with claim 1, further comprising identifying one or more hub residue positions.

4. A method in accordance with claim 3, wherein the one or more hub residue positions are of a rank order in the $40^{th}$ percentile or greater.

5. A method in accordance with claim 1, wherein the Hepatitis C virus is selected from the group consisting of a Hepatitis C virus subtype 1a and a Hepatitis C virus subtype 1b.

6. A method in accordance with claim 1, wherein the therapy is selected from the group consisting of an interferon-based therapy, a guanosine analog-based therapy, and a combination thereof.

7. A method in accordance with claim 6, wherein the antiviral therapy is treatment with ribavirin and pegylated interferon-$\alpha$.

8. A method in accordance with claim 1, wherein the identifying covariance pairs of amino acid residues in each group comprises:
   (i) generating a sequence alignment for the sequences in each group; and
   (ii) calculating the observed minus expected square (OMES) for each amino acid pair.

* * * * *